US009864026B2

United States Patent
Qian et al.

(10) Patent No.: US 9,864,026 B2
(45) Date of Patent: Jan. 9, 2018

(54) WIRELESSLY POWERED MAGNETIC RESONANCE IMAGING SIGNAL AMPLIFICATION SYSTEM

(75) Inventors: Chunqi Qian, Rockville, MD (US); Joe Murphy-Boesch, Rockview, MD (US); Alan Koretsky, Bethesda, MD (US); Stephen John Dodd, Bethesda, MD (US)

(73) Assignee: The Government of The United States of America, as represented by the Secretary, Department of Health and Human Services, Washington, DC (US)

( * ) Notice: Subject to any disclaimer, the term of this patent is extended or adjusted under 35 U.S.C. 154(b) by 1137 days.

(21) Appl. No.: 14/008,133

(22) PCT Filed: Mar. 29, 2012

(86) PCT No.: PCT/US2012/031083
§ 371 (c)(1),
(2), (4) Date: Nov. 15, 2013

(87) PCT Pub. No.: WO2012/135421
PCT Pub. Date: Oct. 4, 2012

(65) Prior Publication Data
US 2014/0066753 A1    Mar. 6, 2014

Related U.S. Application Data

(60) Provisional application No. 61/468,911, filed on Mar. 29, 2011.

(51) Int. Cl.
*A61B 5/00* (2006.01)
*G01R 33/36* (2006.01)
*G01R 33/28* (2006.01)

(52) U.S. Cl.
CPC ..... *G01R 33/3692* (2013.01); *G01R 33/3621* (2013.01); *A61B 5/00* (2013.01); *G01R 33/285* (2013.01)

(58) Field of Classification Search
CPC .... G01R 33/3692; G01R 33/3621; H03F 7/04
See application file for complete search history.

(56) References Cited

U.S. PATENT DOCUMENTS

2003/0227289 A1  12/2003  Heid et al.
2006/0279284 A1* 12/2006  Vaughan ............... A61B 5/05
                                                324/318

(Continued)

OTHER PUBLICATIONS

Qian, et al., Integrated Detection, Amplification and Wireless transmission of MRI Signals Using a Parametric Amplifier, Proceedings of the International Society for Magnetic Resonance in Medicine, 19th Annual Meeting and Exhibition, Montreal, Quebec, May 7-13, 2011, Apr. 23, 2011, p. 626.

*Primary Examiner* — Serkan Akar
(74) *Attorney, Agent, or Firm* — Polsinelli PC; Ron Galant

(57) ABSTRACT

An implantable parametric circuit enables local signal amplification and wireless transmission of RF signals in connection with magnetic resonance imaging systems. The parametric circuit detects RF signal detected during magnetic resonance imaging procedure, amplifies the detected RF signal, and transmits the amplified RF signal in a wireless manner to an external pick-up coil. The parametric amplifier is also configured to use another RF signal generated by an external source as the primary power source. As a result, implanted or catheter coils could be used as a wireless signal transducer without the need for a battery or a power connection.

6 Claims, 7 Drawing Sheets

(56) References Cited

U.S. PATENT DOCUMENTS

2010/0253349 A1   10/2010  Cork et al.
2012/0062230 A1*  3/2012   Vaughan, Jr. ...... G01R 33/3415
                                                        324/318

* cited by examiner

WIRELESSLY POWERED MAGNETIC RESONANCE IMAGING SIGNAL AMPLIFICATION SYSTEM

BACKGROUND

Magnetic resonance imaging (MRI) is a well-established medical imaging and diagnostic tool. A great deal of current activity and research relates to interventional and/or intraoperative procedures conducted under MRI guidance (iMRI). For example, in many interventional and intraoperative procedures under MRI guidance, surgical devices such as long needles, guidewires, and catheters are used and it is advantageous for a surgeon to be able to image the local tissue and locate such instruments in conjunction with the magnetic resonance image. To achieve active device profiling during real time MRI, interventional devices have been provided with a radio frequency (RF) antenna, more particularly an RF coil, in the device.

The RF or receive coil is typically located at the distal end of the catheter or other device and receives a signal from excited protons of blood or tissue of its vicinity when they return to equilibrium. The RF coil then sends an electrical signal directly to the MRI scanner by way of an attached coaxial cable. The coaxial cable is typically a very thin coaxial cable that runs through a lumen in the catheter. The presence of long conductive objects, such as coaxial cables, can lead to heating in such RF coils. Medical studies indicate that this effect is due to coupling of the RF field from the MRI system, primarily to the long cable ("Reduction of Resonant RF Heating in Intravascular Catheters Using Coaxial Chokes", Mark E. Ladd et al., Magnetic Resonance in Medicine 43:61-5-619 (2000); "RF Safety of Wires in Interventional MRI: Using a Safety Index", Christopher J. YEUNG et al., Magnetic Resonance in Medicine 47:187-193 (2002); "RF Heating Due to Conductive Wires During MRI Depends on the Phase Distribution of the Transmit Field", Christopher J. YEUNG et al., Magnetic Resonance in Medicine 48:1096-1098 (2002); and "Safety of MRI-Guided Endovascular Guidewire Applications", Chia-Ying LIU et al. Journal of Magnetic Resonance Imaging 12:75-78 (2000)). These studies indicate that long transmission lines, even without the RF coil, show significant heating, whereas, RF coils without the cable show no heating.

To avoid heating caused by long transmission lines, there have been attempts to wirelessly transmit MRI signals received at RF coils. In most cases, the wireless transmission of signal relies on passive inductive coupling, a process which could lead to excessive sensitivity loss if the magnitude of inductive coupling is small. To improve the detection sensitivity through inductive coupling, a low noise preamplifier is sometimes connected to the RF coil. The preamplifier is used to amplify the received RF signal prior to the wireless transmission to the receiver connected to the MRI scanner. However, most transistor based low-noise amplifiers require a local DC power source. In the case of implanted or catheter coils, it can be difficult, impracticable, and/or expensive to provide a local DC power source without a wire connection.

SUMMARY

According to one aspect, a system is provided for improved implantable MRI compatible devices that enable wireless transmission of RF signals and that do not require a local or DC power source.

According to another aspect, a system is provided for wireless amplification of an RF signal generated by a magnetic resonance imaging (MRI) device. The system includes an ingestible device that includes a pre-amplification circuit. The pre-amplification circuit includes at least one resonator that resonates at a first frequency in response to a first RF signal generated by a magnetic resonance imaging device. The at least one resonator generates an input current at the first frequency. The at least one resonator resonates at a second frequency in response to a second RF signal generated at an external frequency generator second RF signal to generate a pumping current at the second frequency. The at least one resonator resonates at a third frequency to generate a third RF signal at the third frequency. The pre-amplification circuit also includes a varactor to generate an amplified current having the third frequency based on the input current and the pumping current the amplified current. The system also includes an external coil to: receive the third RF signal; and to transmit the third RF signal to an MRI device for image processing.

According to another aspect, a system is provided for wireless amplification of an RF signal generated by a magnetic resonance imaging (MRI) device. The system includes an interventional device for introduction into a subject. The interventional device includes a pre-amplification circuit. The pre-amplification circuit includes at least one resonator that resonates at a first frequency in response to a first RF signal generated by a magnetic resonance imaging device. The at least one resonator generates an input current at the first frequency. The at least one resonator resonates at a second frequency in response to a second RF signal generated at an external frequency generator second RF signal to generate a pumping current at the second frequency. The at least one resonator resonates at a third frequency to generate a third RF signal at the third frequency. The pre-amplification circuit also includes a varactor to generate an amplified current having the third frequency based on the input current and the pumping current the amplified current. The system also includes an external coil to: receive the third RF signal; and to transmit the third RF signal to an MRI device for image processing.

According to another aspect, an interventional device for introduction into a subject is provided. The interventional device includes a pre-amplification circuit. The pre-amplification circuit includes at least one resonator that receives a first RF signal from a magnetic resonance imaging device. The first RF signal has a first frequency. The at least one resonator resonates at the first frequency to generate an input current at the first frequency. The at least one resonator receives a second RF signal at a second frequency from an external frequency generator and resonates at the second frequency in response to the second RF signal to generate a pumping current at the second frequency. The at least one resonator resonates at a third frequency to generate a third RF signal at the third frequency. The pre-amplification circuit also includes a varactor to generate an amplified current having the third frequency based on the input current and the pumping current the amplified current. The at least one resonator further transmits the third RF signal for image processing.

DETAILED DESCRIPTION

Medical devices, such as catheters, guidewires, endoscopes, and/or other interventional surgical devices (interventional devices), are often inserted into the body of a subject undergoing imaging analysis with a magnetic resonance imaging (MRI) system, such as a MRI scanner. The wire-like conductive structures connecting the interventional device interact with the radio-frequency fields in the MRI system, and under certain conditions an RF signal, such as electrical currents and/or voltages can be induced in these structures. The RF current induced on the connection wire can cause local heating of tissue adjacent to the interventional device during the MRI procedure, which can potentially lead to undesired tissue damage within the subject.

Aspects of the wirelessly powered amplification system and method described herein minimize RF heating and enable operation of a parametric amplifier by detecting and amplifying RF signals during MRI procedure and then wirelessly transmitting the amplified RF signals for analysis. Aspects of the wirelessly powered amplification system enable operation of an amplification circuit without requiring a physical connection to a power source. For example, the parametric amplifier can be embodied in an implantable/ingestible/in vivo system that enables wireless transmitting amplified RF signals for analysis of a subject, such as a patient.

Figure 1:
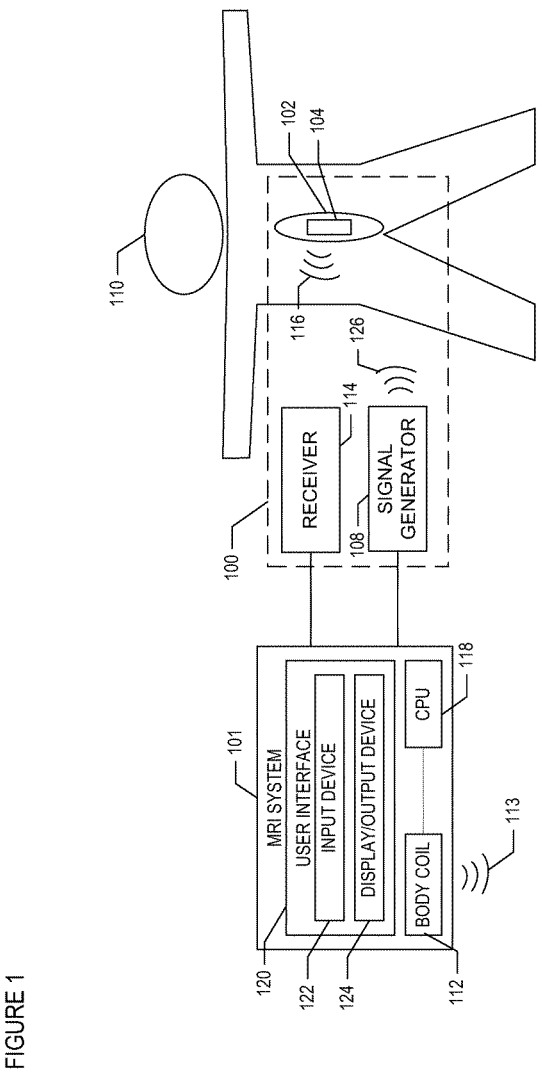
FIG. 1 is a block diagram that depicts an exemplary embodiment of the wirelessly powered amplification system.

FIG. 1 depicts an exemplary aspect of the wirelessly powered amplification system (WPAS) 100. The WPAS 100 is connected to a MRI system 101 and an interventional device 102. The WPAS 100 includes a pre-amplification circuit 104, a RF receiver 114, and a signal generator 108.

The MRI system 101 is, for example, a MRI scanner device that enables the visualization of organs, organ function, and/or other tissue within a body of a subject 110, such as a patient. The MRI system 101 includes a primary magnet (not shown) that generates a uniform magnetic field that is applied across the body of the subject 110 under observation. The MRI system 101 also includes smaller gradient magnets (not shown) that allow the magnetic field to be altered very precisely. The gradient magnets allow image "slices" of the body to be created. By altering the gradient magnets, the magnetic field can be specifically encoded on a selected part of the body.

After the subject 110 is properly positioned for analysis by the MRI system 101, a body coil 112 of the MRI system 101 emits a radio frequency (RF) radiation field signal, as indicated by reference character 113. The RF signal 113 causes the nuclei within the body of the subject 110 to change their spin orientation and precess. The frequency of the energy at which this transition occurs is known as the Larmor Frequency. When the body coil 112 is not providing the RF radiation field, the spin of hydrogen nuclei change back to a lower energy state and reemits the electromagnetic energy at the RF wavelength.

During MRI analysis of the subject 110, the interventional device 102 can be introduced into the subject 110 via, for example, a vascular structure within the body of the subject 110. According to the illustrated aspect, the interventional device 102 is an ingestible device, such as an ingestible capsule for use in examining the gastrointestinal tract. According to another aspect, the interventional device 102 includes flexible tubing or a lumen that extends along the length of the interventional device 102.

Regardless of the device type, the interventional device 102 is configured to include the pre-amplification circuit 104. As explained in more detail below, the pre-amplification circuit 104 includes a first resonator that is matched and tuned to the Larmor frequency of the MRI system 101 to, for example, detect the RF energy signal emitted by the spin precession of the atoms within surrounding tissue and generate an input current signal. The pre-amplification circuit 104 further amplifies the detected RF signal and then wirelessly transmits the amplified RF signal to a receiver 114, such as external pick-up coil.

According to one aspect, the receiver 114 enables viewing of the interventional device 102 within the body of a subject 110 undergoing MRI analysis. For example, the amplified RF signal, as indicated by 116, received by the receiver 114 is transmitted to the MRI system 101 to be processed and combined in an appropriate way for imaging.

For example, the MRI system 101 includes a central processing unit 118, such as a computer, processor, or other processing device, to receive and process the amplified RF signal 116 to create images to display via a user interface 120. The user interface 120 includes, for example, one or more input devices 122, along with one or more displays or output devices 124. In a typical application, the input device 122 will include a conventional operator keyboard, or other operator input devices for selecting image types, image slice orientations, configuration parameters, and so forth. The display/output device 124 will typically include a computer monitor for displaying the operator selections, as well as for viewing scanned and reconstructed images. Such devices may also include printers or other peripherals for reproducing hard copies of the reconstructed images. The central processing unit 118 is also communicatively linked with the user interface 120 to receive input data from a user and/or to provide image data to the user.

According to one aspect, the central processing unit 118 processes the amplified RF signal 116 to perform 2D Fourier transforms to convert the acquired data from the time domain to the frequency domain, and to reconstruct the data into a meaningful image. The amplified RF signal 116 may indicate different resonance characteristics for different tissue types. For example, the different resonance characteristics produced from a particular organ are displayed in an image in different of shades of grey, such that some body tissues show up darker or lighter as compared to other body tissues. As another example, the different resonance characteristics produced from a particular organ can be displayed in an image as different colors or displayed as different contrast of a particular color.

The pre-amplification circuit 104 is powered via an external source, such as the RF signal generator 108 that produces a pumping RF signal, as indicated by 126, at a desired pumping frequency. The pre-amplification circuit 104 includes a second resonator that is matched and tuned to the pumping frequency to generate a pumping current signal. As explained in more detail below, the pumping current signal is used to drive a non-linear capacitor, such as a varactor, to perform frequency mixing and to produce the amplified RF signal 116 as explained in more detail below in reference to FIG. 2.

Notably, the pre-amplification circuit 104 uses the RF pumping signal 126 as the primary power source, rather than the DC current. As a result, the pre-amplification circuit 104 enables visualization of the interventional device 102 within the subject 110 without the need for a local battery or a power connection.

Figure 2A:
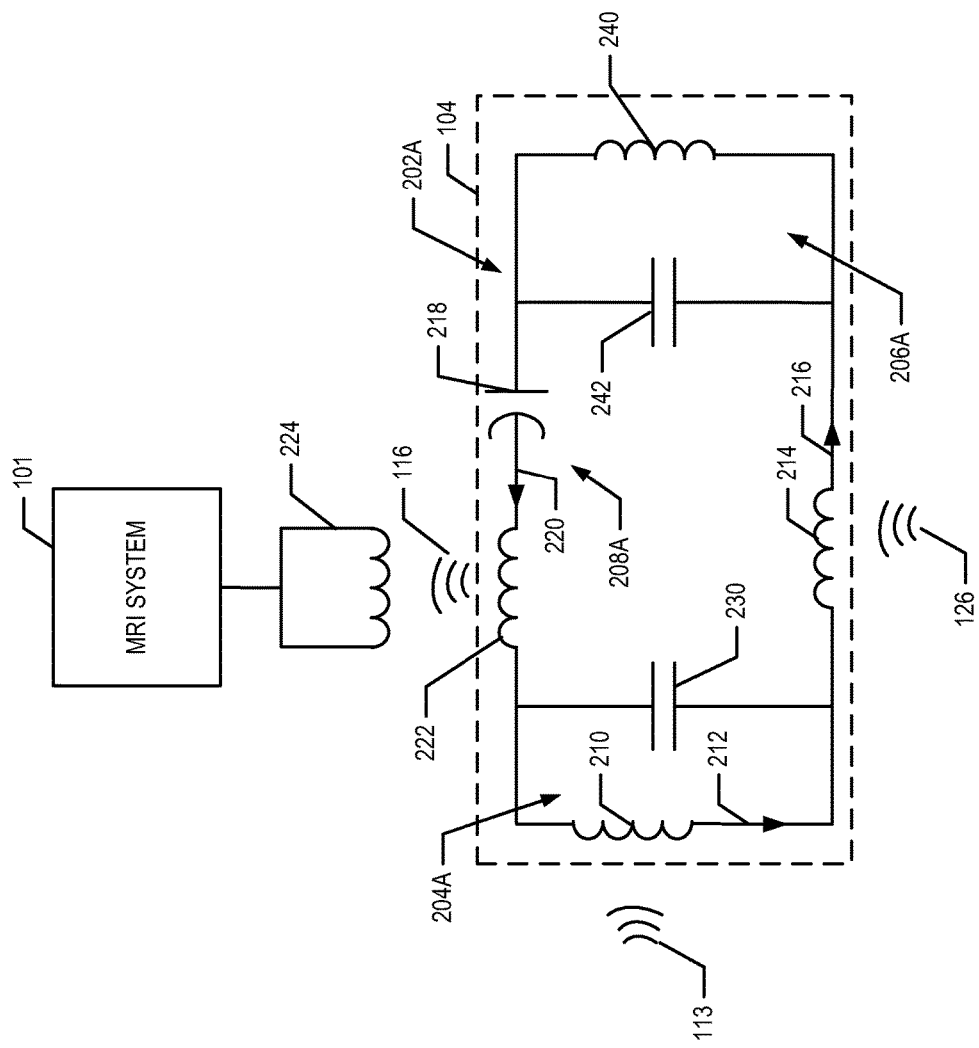
FIGS. 2A-2E depicts exemplary circuit diagrams of pre-amplification circuits according to aspect of the wirelessly powered amplification system.

FIG. 2A depicts an exemplary schematic circuit diagram of the pre-amplification circuit 104. According to this aspect, the pre-amplification circuit 104 is implemented with a parametric amplifier 202. The parametric amplifier 202A includes nonlinear components, and generates the amplified RF signal 116 with a power gain by mixing an RF input signal (e.g., signal 113) at a lower frequency with a pumping signal (e.g., signal 126) at a higher frequency. In this particular aspect, the parametric amplifier 202A is a triple frequency resonator that includes three L-C meshes 204A, 206A, and 208A that are each configured to resonate at three different frequencies. Stated differently, each of the L-C meshes 204A, 206A, and 208A correspond to an individual resonator.

The L-C mesh 204A includes resonating components that resonate at a desired frequency, $\omega 1$. For example, the resonating components such as inductor 210 and capacitor 230, are selected so that the entire circuit 104 resonates (i.e., conducts current) at the spin precession frequency, such as 132.1 MHz. As explained above, the source of the 132.1 MHz frequency may be, for example, an RF energy signal emitted by the precessing of the atomic spins within surrounding tissue. For example, the body coil 112 of the MRI 102 excites the nuclei spins to introduce Larmor precession of spins and the resonation components of the L-C mesh 204 couples with the nuclei spins to acquire the RF input signal 113. Thus, during the precessing of atoms an input current signal 212 is induced at the resonating components at input frequency $\omega 1$.

The L-C mesh 206A includes resonating components that resonates when receiving pumping signal 126 at a pumping frequency, $\omega 3$. For example, the L-C mesh 206A includes as inductor 240 and capacitor 242. The pumping frequency is provided by an external source, such as RF signal generator. During application of the pumping frequency, a pumping current 216 is induced at another resonating component, inductor 214. The inductors 214, 240 and capacitor 242 are selected so that the entire circuit 104 resonates at a pumping frequency, such as 633.9 MHz. The majority of the pumping current 216 flows through a varactor 218. The varactor 218 has a high-Q at zero biased condition, and it performs frequency mixing between the input current 212 at the $\omega 1$ frequency and the pumping current 216 at the $\omega 3$ frequency, to generate an amplified current signal 220 at the difference frequency $\omega 2$.

The L-C mesh 208A includes resonating components, such as an inductor 222 and the varactor 218, such that the amplified current signal 220 flows through the resonating components and generates an amplified output signal (e.g., amplified RF signal 116). According to one aspect, the inductor 222 is a rectangular copper loop. A receiving coil 224 (e.g., receiver 114) can be positioned external to the body and can be configured to resonate at the difference frequency at $\omega 2$ to inductively pick-up the amplified up converted output signal and provide the amplified output signal to the MRI device for processing. According to one aspect, the parametric circuit 104 has a noise level of approximately 1.0 dB and produces amplified output signal that has a stable gain up to 27 dB.

Figure 2B:
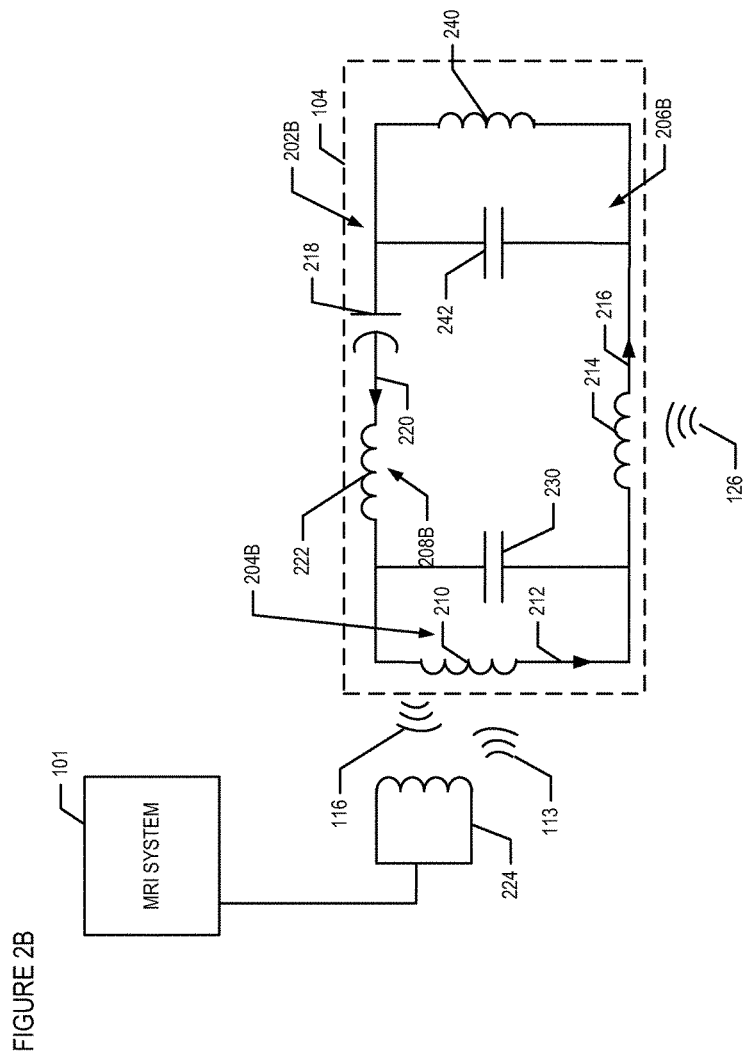

FIG. 2B depicts another exemplary schematic circuit diagram of the pre-amplification circuit 104. In this particular aspect, the pre-amplification circuit 104 is also implemented with the parametric amplifier 202. In this aspect, however, the receiver coil 224 is coupled to a different portion of the parametric amplifier 202. In particular, the receiving coil 224 (e.g., receiver 114) can be configured to resonate at the frequency at $\omega 1$ to inductively pick-up the amplified output signal and provide the amplified output signal 116 to the MRI device for processing. Thus, in this particular aspect, although the parametric amplifier 202B includes three L-C meshes 204B, 206B, and 208B, only two frequencies at L-C meshes 204B and 206B are used for signal acquisition.

Figure 2C:
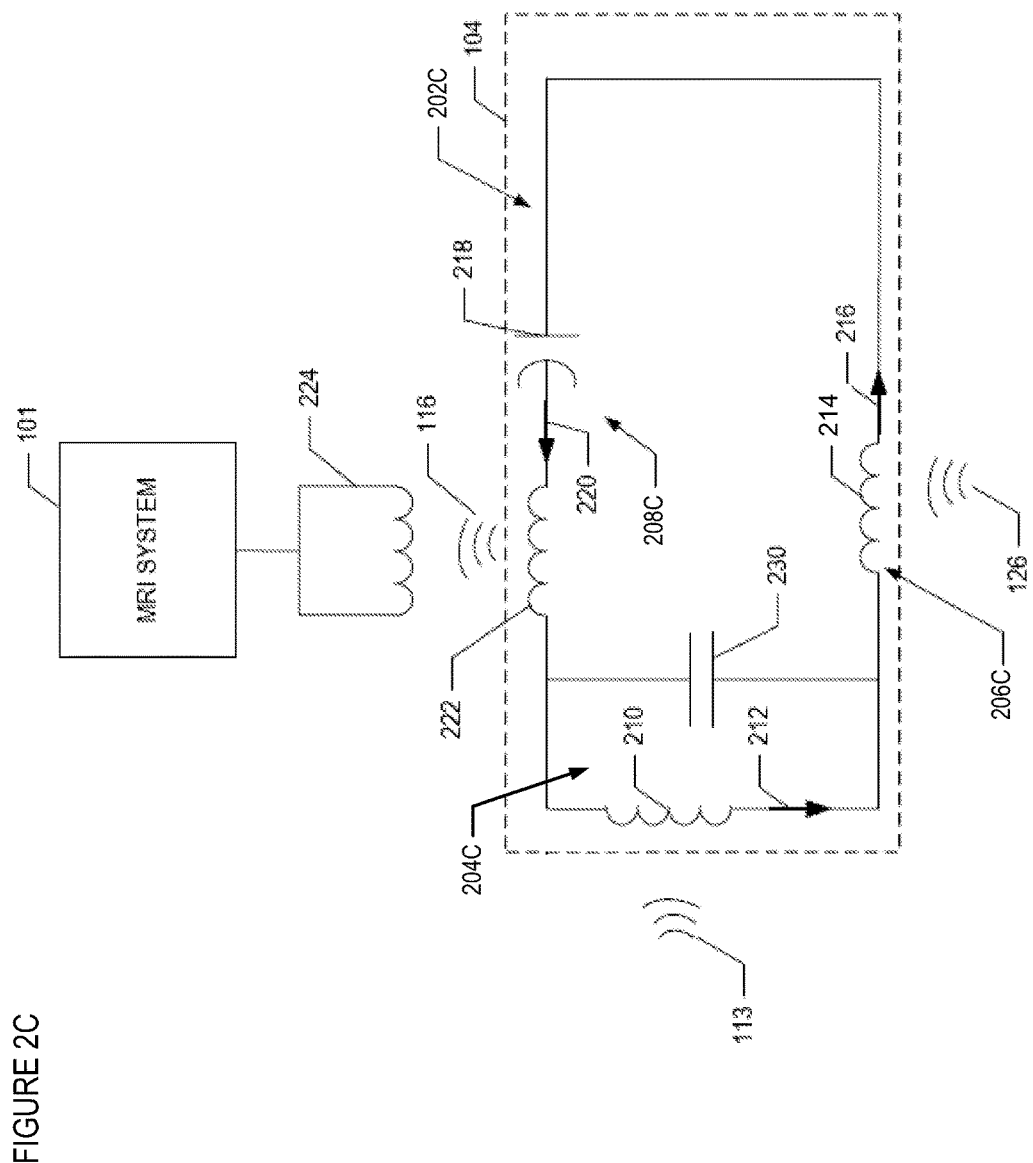

FIG. 2C depicts another exemplary schematic circuit diagram of the pre-amplification circuit 104. In this particular aspect, the parametric amplifier 202C is a double frequency resonator that includes L-C meshes 204C, 208C that each resonate at a different frequency. This double frequency resonator configuration can be used, for example, when the signal frequency $\omega 1$ is close but not equal to the difference frequency $\omega 2$.

According this aspect, the L-C mesh 204C includes resonating components that resonate at a desired frequency, $\omega 1$. For example, the resonating components such as inductor 210 and capacitor 230, are selected so that the entire circuit 104 resonates (i.e., conducts current) at the spin precession frequency, such as 499.55 MHz.

As described above, the pumping frequency is provided by an external source, such as RF signal generator, at a pumping frequency, $\omega 3$. During application of the pumping frequency, the pumping current 216 is induced at inductor 214. For example, the value of the resonating components such as inductor 214 is selected so that the entire circuit 104 resonates at a pumping frequency, such as 999.16 MHz. Notably, the inductor 240 and capacitor 242, as depicted in FIGS. 2A and 2B, are not included in embodiment depicted in FIG. 2C.

The majority of the pumping current 216 flows through a varactor 218. The varactor 218 has a high-Q at zero biased condition, and it performs frequency mixing between the input current 212 at the $\omega 1$ frequency and the pumping current 216 at the $\omega 3$ frequency, to generate an amplified current signal 220 at the difference frequency $\omega 2$. The varactor 218 is selected such that the difference frequency $\omega 2$ is nearly equal to the $\omega 1$ frequency. For example, $\omega 2$ in this case is 499.61 MHz, which is only 60 kHz higher than $\omega 1$ at 499.55 MHz.

The L-C mesh 208C includes resonating components, such as an inductor 222 and the varactor 218, such that the amplified current signal 220 flows through the resonating components and generates the amplified output signal (e.g., amplified RF signal 116). According to one aspect, the inductor 222 is a rectangular copper loop. A receiving coil 224 (e.g., receiver 114) can be positioned external to the body and can be configured to resonate at the difference frequency at $\omega 2$ to inductively pick-up the amplified up converted output signal and provide the amplified output signal to the MRI device, or other measurement device for processing.

Figure 2D:
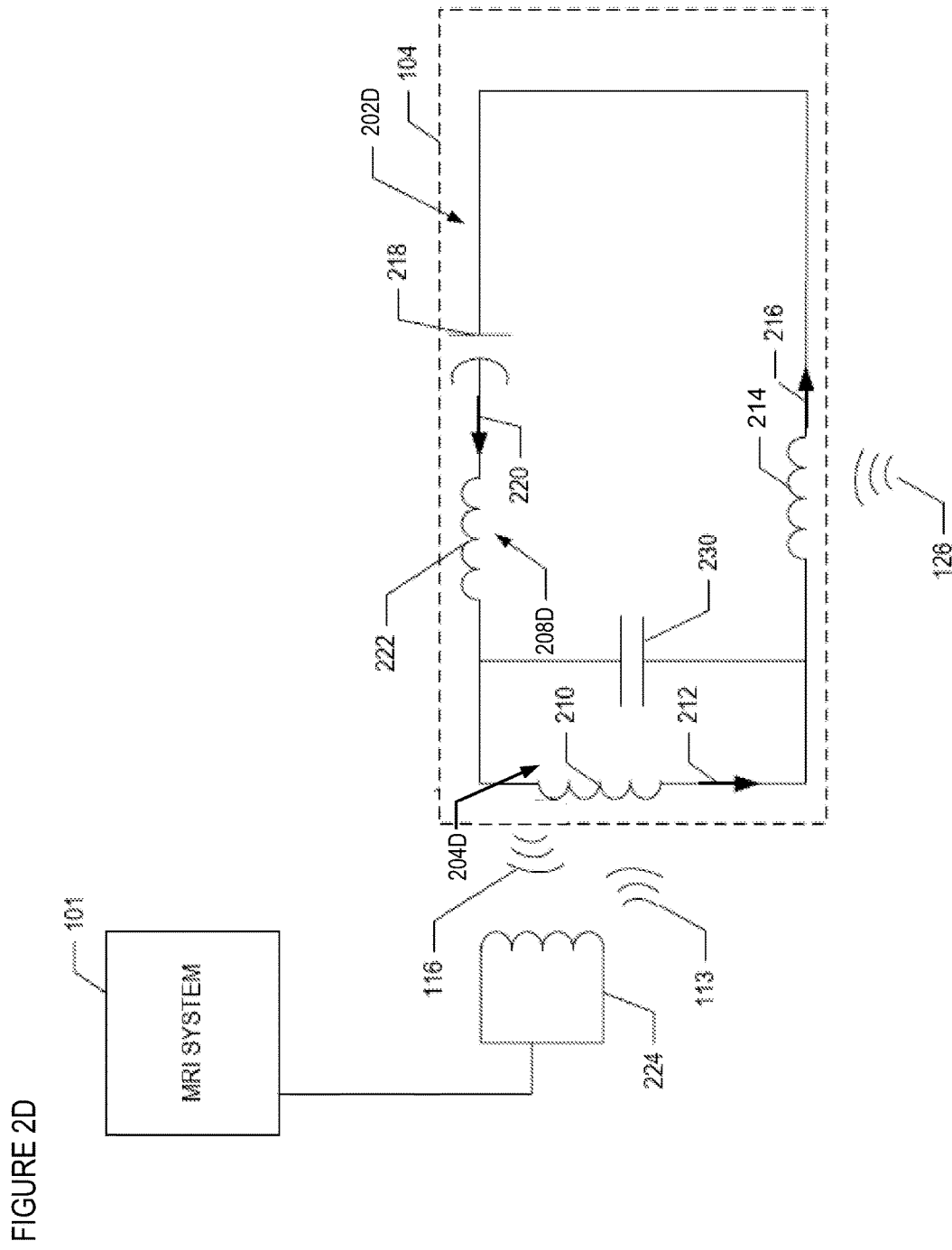

FIG. 2D depicts another exemplary schematic circuit diagram of the pre-amplification circuit 104. In this particular aspect, the parametric amplifier 202D is a double frequency resonator. In this aspect, the pre-amplification circuit 104 is substantially the same as the pre-amplification circuit depicted in FIG. 2C. In particular, the pre-amplification circuit 104 includes two L-C meshes 204D and 208D that are configured the same as L-C meshes 204C and 208C, respectively. In this aspect, however, the receiver coil 224 is coupled to a different portion of the parametric amplifier 202D. In particular, the receiving coil 224 (e.g., receiver 114) can be configured to resonate at the frequency at ω1 (e.g., Larmor frequency), to inductively pick-up the amplified output signal and provide the amplified output signal to the MRI device for processing. The pumping frequency is provided by an external source, such as RF signal generator, at a pumping frequency, ω3.

Figure 2E:
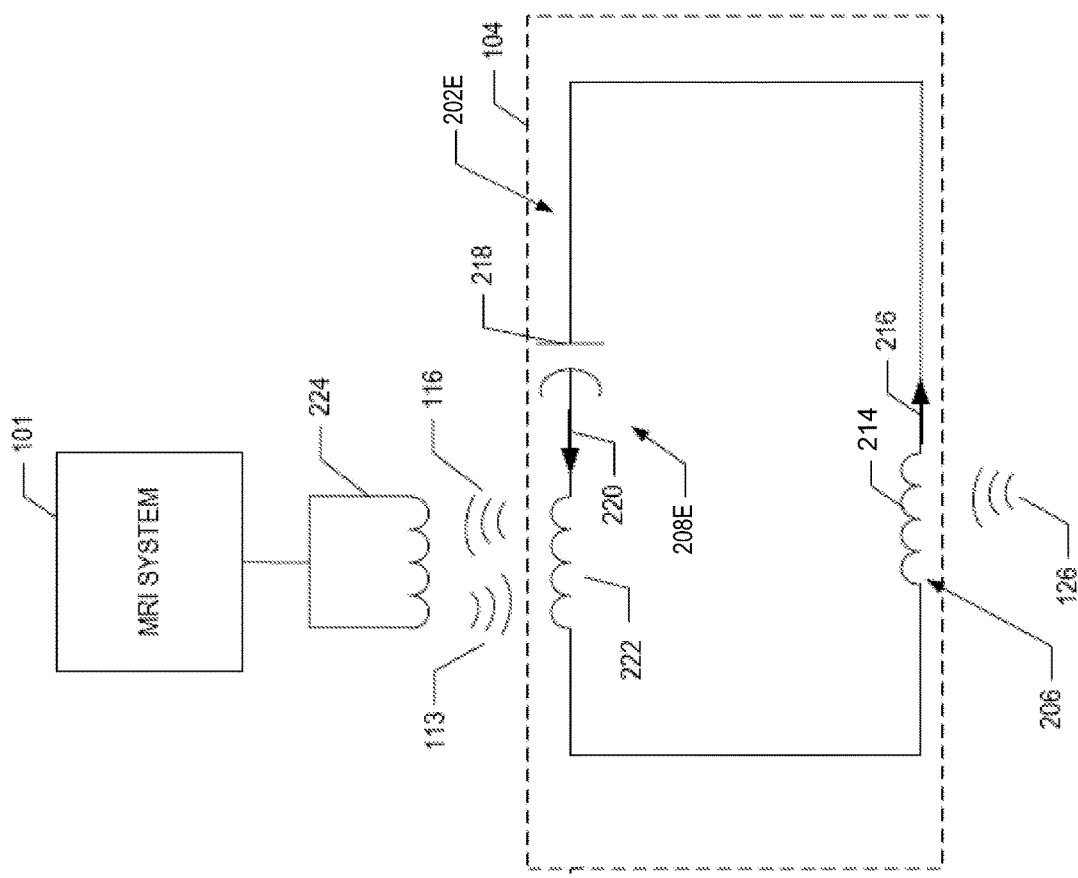

FIG. 2E depicts another exemplary schematic circuit diagram of the pre-amplification circuit 104. In this particular aspect, the parametric amplifier 202E is a single frequency resonator that includes L-C mesh 208C. This single frequency resonator configuration can be used, for example, when the three frequencies ω1, ω2, and ω3 are close but not equal to each other. For example, ω1 is 499.55 MHz, ω2 is 499.61 MHz, and ω3 is 499.58 MHz.

As described above, the pumping frequency is provided by an external source, such as RF signal generator, at a pumping frequency, ω3. During application of the pumping frequency, the pumping current 216 is induced at inductor 214. For example, the value of the resonating components such as inductor 214 is selected so that the entire circuit 104 resonates at a pumping frequency, such as 499.58 MHz. Notably, the inductor 240 and capacitor 242, as depicted in FIGS. 2A and 2B, are not included in embodiment depicted in FIG. 2C.

The L-C mesh 208E includes resonating components, such as an inductor 222 and the varactor 218, such that the amplified current signal 220 flows through the resonating components and generates the amplified output signal (e.g., amplified RF signal 116). According to one aspect, the inductor 222 is a rectangular copper loop. A receiving coil 224 (e.g., receiver 114) can be positioned external to the body and can be configured to resonate at the frequency at ω1 to inductively pick-up the amplified up converted output signal and provide the amplified output signal 116 to the MRI device, or other measurement device for processing. In this aspect, because ω1 and ω2 are substantially same frequencies, the same receiving coil 224 can receive both signals. External circuitry (not shown) can be used to separate these two signals.

Figure 2F:
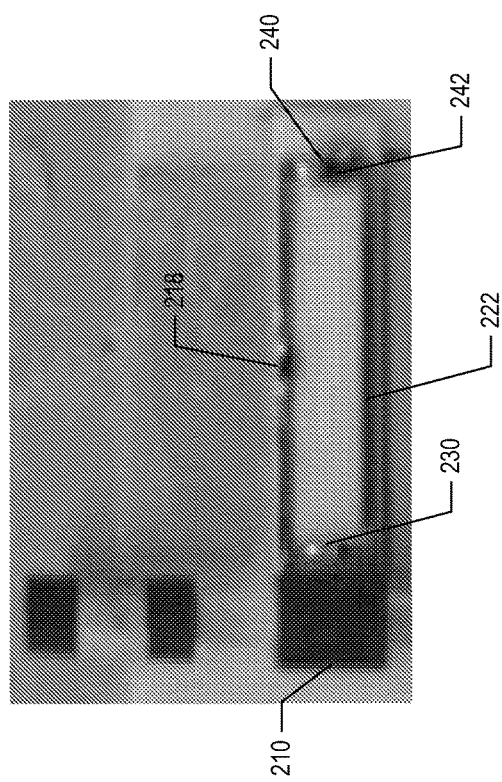
FIG. 2F depicts an exemplary circuit pre-amplification circuit according to aspect of the wirelessly powered amplification system.

FIG. 2F depicts an exemplary pre-amplification circuit 104 that comprises the resonating components, such as described above in reference to FIG. 2A.

Figure 3:
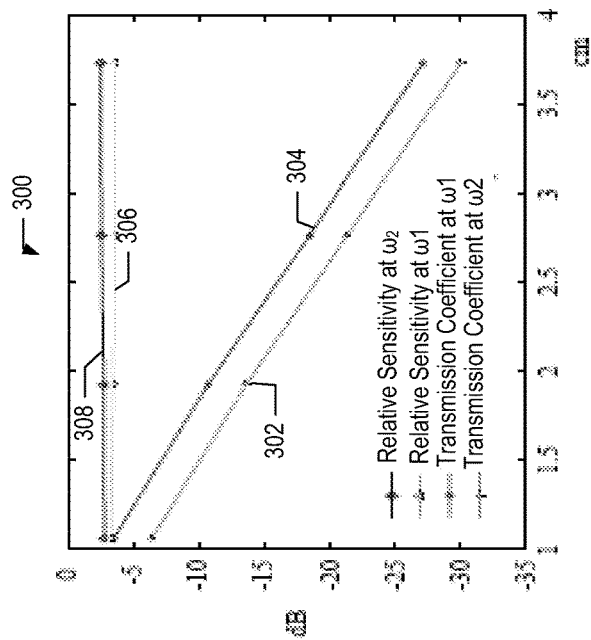
FIG. 3 is a graph illustrating sensitivity profiles.

FIG. 3 is a graph 300 that depicts enhanced normalized sensitivity with and without parametric amplification between the resonator and an external loop at different distance separations. In particular, graph 300 depicts power sensitivity profiles 302, 304, 306, and 308 that correspond to an exemplary resonator output loop (e.g., receiver) having dimensions 6.5×6.5 mm². The bottom two profiles 302, 304 represent the detection sensitivity obtained without parametric amplification at ω2 and ω1 respectively. The top two profiles 306, 308 represent the substantially enhanced detection sensitivity obtained with parametric amplification at ω1 and ω2 respectively. Thus, there is improved sensitivity at the output loop when parametric amplification is used.

Those skilled in the art will appreciate that variations from the specific embodiments disclosed above are contemplated by the invention. The invention should not be restricted to the above embodiments, but should be measured by the following claims.

The invention claimed is:

1. A system for wireless amplification of a first radio frequency (RF) signal generated by a magnetic resonance imaging device, wherein the first RF signal has a first frequency, the system comprising:
   an external frequency generator to generate a second RF signal at a second frequency;
   an ingestible device comprising a pre-amplification circuit, the pre-amplification circuit consisting of three loop current (L-C) meshes, wherein:
      the first L-C mesh consists of a first inductor and a first capacitor, to resonate at the first frequency and generate an input current at the first frequency in response to the first RF signal;
      the second L-C mesh consists of a second inductor and a second capacitor, to resonate at the second frequency in response to the second RF signal to generate a pumping current at the second frequency; and
      the third L-C mesh consists of the first capacitor, the second capacitor, a third inductor, a varactor, and optionally a fourth inductor, to resonate at a third frequency in response to an amplified current to generate a third RF signal at the third frequency; and
   an external coil to:
   receive the third RF signal; and
   transmit the third RF signal to the magnetic resonance imaging device for image processing;
   wherein the varactor is a zero biased nonlinear capacitor and generates the amplified current based on the input current and the pumping current, wherein the amplified current has the third frequency, and wherein the system wirelessly amplifies the first RF signal.

2. The system of claim 1 wherein the first resonator acquires the first RF signal from tissue surrounding the ingestible device to resonate at the first frequency.

3. The system of claim 1 wherein the second resonator inductively couples to the external frequency generator to resonate at the second frequency.

4. The system of claim 1 wherein the external coil inductively couples to the third resonator and resonates at the third frequency.

5. The system of claim 1 wherein the third RF signal corresponds to an amplification of the first RF signal.

6. The system of claim 1 wherein the first frequency and the third frequency are substantially equal to a particular frequency value and the second frequency is equal to a different particular frequency value.

* * * * *